(12) United States Patent
Hoptroff et al.

(10) Patent No.: US 11,224,568 B2
(45) Date of Patent: Jan. 18, 2022

(54) ANTIMICROBIAL CLEANSING COMPOSITION

(71) Applicant: Conopco, Inc., Englewood Cliffs, NJ (US)

(72) Inventors: Michael John Hoptroff, Bebington (GB); Zhenyu Tang, Shanghai (CN)

(73) Assignee: CONOPCO, INC., Englewood Cliffs, NJ (US)

( * ) Notice: Subject to any disclaimer, the term of this patent is extended or adjusted under 35 U.S.C. 154(b) by 212 days.

(21) Appl. No.: 16/304,663

(22) PCT Filed: May 15, 2017

(86) PCT No.: PCT/EP2017/061622
§ 371 (c)(1),
(2) Date: Nov. 26, 2018

(87) PCT Pub. No.: WO2017/202636
PCT Pub. Date: Nov. 30, 2017

(65) Prior Publication Data
US 2020/0323760 A1   Oct. 15, 2020

(51) Int. Cl.
| A61K 8/73 | (2006.01) |
| A61K 8/27 | (2006.01) |
| A61K 8/34 | (2006.01) |
| A61K 8/46 | (2006.01) |
| A61K 8/49 | (2006.01) |
| A61K 8/58 | (2006.01) |
| A61K 8/67 | (2006.01) |
| A61Q 5/00 | (2006.01) |
| A61Q 5/02 | (2006.01) |
| A61Q 17/00 | (2006.01) |

(52) U.S. Cl.
CPC ............... *A61K 8/737* (2013.01); *A61K 8/27* (2013.01); *A61K 8/347* (2013.01); *A61K 8/463* (2013.01); *A61K 8/4933* (2013.01); *A61K 8/585* (2013.01); *A61K 8/675* (2013.01); *A61Q 5/006* (2013.01); *A61Q 5/02* (2013.01); *A61Q 17/005* (2013.01); *A61K 2800/10* (2013.01); *A61K 2800/5426* (2013.01)

(58) Field of Classification Search
CPC .......... A61K 8/737; A61K 8/27; A61K 8/347; A61K 8/4933; A61K 8/675; A61K 2800/10; A61K 2800/5426; A61Q 5/006; A61Q 5/02; A61Q 17/005
See application file for complete search history.

(56) References Cited

U.S. PATENT DOCUMENTS

| 6,190,674 B1 | 2/2001 | Beerse et al. |
| 9,132,103 B2 | 9/2015 | Medepalli et al. |
| 2004/0213751 A1* | 10/2004 | Schwartz ............... A61P 31/00 424/70.1 |
| 2006/0013796 A1 | 1/2006 | Chandra |
| 2006/0165616 A1 | 7/2006 | Brock et al. |
| 2013/0150338 A1* | 6/2013 | Ananthapadmanabhan ................ A61K 8/361 514/188 |
| 2013/0296289 A1* | 11/2013 | Hall ................ A61K 8/4933 514/188 |
| 2015/0071977 A1* | 3/2015 | Dihora ................ A61Q 5/02 424/401 |
| 2016/0143825 A1 | 5/2016 | Pesaro et al. |
| 2018/0338494 A1 | 11/2018 | Agarkhed et al. |
| 2019/0264146 A1 | 8/2019 | Agarkhed et al. |

FOREIGN PATENT DOCUMENTS

| CN | 1264294 | 8/2000 |
| CN | 1758895 | 4/2006 |
| CN | 102510723 | 6/2012 |
| CN | 103052427 | 4/2013 |
| CN | 104473810 | 4/2015 |
| CN | 108289444 | 7/2018 |
| CN | 108366925 | 8/2018 |
| JP | 2004155901 | 6/2004 |
| JP | 2005538135 | 12/2005 |
| JP | 2008110999 | 5/2008 |
| JP | 2013155168 | 8/2013 |
| JP | 2013544266 | 12/2013 |
| JP | 2014088373 | 5/2014 |
| JP | 2016504301 | 2/2016 |
| KR | 20150145577 | 12/2015 |
| WO | WO0130311 | 5/2001 |
| WO | WO2004006876 | 1/2004 |
| WO | WO2010046238 | 4/2010 |
| WO | WO2012072424 | 12/2012 |
| WO | WO2014093074 | 6/2014 |
| WO | WO2016012797 | 1/2016 |
| WO | WO2017089104 | 6/2017 |
| WO | WO2017089108 | 6/2017 |

OTHER PUBLICATIONS

Claims of EP2605832 A1 2013 Ananthapadmanabhan et al.*
Description of EP2605832 A1 2013 Ananthapadmanabhan et al.*
Claims of EP2645986 A2 2013 Hall et al.*
Description of EP2645986 A2 2013 Hall et al.*
https://www.australab.com/blog/make-shampoo-hair-care/), Mar. 2016.*
IPRP2 in PCTEP2017061622; Sep. 3, 2018.
Search Report and Written Opinion in PCTEP2017061622; dated Jul. 28, 2017.
Written Opinion in PCTEP2017061622; dated May 17, 2018.
Search Report & Written Opinion in EP16177939; dated Nov. 18, 2016.
Song Liya et al.; Research and Development of Plant Effect Additives for Cosmetics; Cosmetic 2011; pp. 208-210 (with original in Chinese + English translation of relevant portions only); China Light Industry Pres.
Wu Guoguang, et al.; Chemical Specialized Experiments; 2005; 117-118 (with original in Chinese + English translation of relevant portions only); China University of Mining and Technoogy Press; China.

* cited by examiner

*Primary Examiner* — Blessing M Fubara
(74) *Attorney, Agent, or Firm* — Foley & Lardner LLP

(57) ABSTRACT

This invention relates to an antimicrobial cleansing composition, especially one which provides synergistic anti-dandruff efficacy. This is achieved through a judicious combination of anti-dandruff agent zinc pyrithione and thymol in a composition comprising synthetic anionic surfactant.

12 Claims, No Drawings

ANTIMICROBIAL CLEANSING COMPOSITION

CROSS REFERENCE TO RELATED APPLICATIONS

The present application is a U.S. National Phase Application under 35 U.S.C. § 371 of International Application No. PCT/EP2017/061622 filed May 15, 2017, which claims priority to International Application No. PCT/CN2016/083751 filed May 27, 2016 and EP Application No. 1617739.2 filed Jul. 5, 2016, the contents of which are incorporated herein in their entireties.

FIELD OF THE INVENTION

This invention relates to a hair care composition. The invention more particularly relates to a personal care composition which provides anti-dandruff efficacy. It more particularly relates to a cleansing composition comprising anti-microbial actives which interact in the presence of synthetic anionic surfactant to deliver this benefit.

BACKGROUND OF THE INVENTION

The invention relates to hair care compositions. Hair care compositions generally provide cleansing or conditioning benefits or a combination of the two. Such compositions typically comprise one or more cleansing surfactants which generally aid in cleaning the hair and/or the scalp free of undesirable soil, particles, and fatty matter.

Additionally, anti-dandruff benefit has been provided through hair care compositions. Dandruff is an issue that affects many people globally. The condition is manifested by the shedding of clumps of dead skin cells from the scalp. These are white in colour and provide an aesthetically displeasing appearance. A factor that contributes to dandruff are certain members of the *Malassezia* yeasts. To combat these, anti-dandruff products have been developed in the form of hair cleansing shampoos. An example of a known anti-dandruff shampoo comprises sodium lauryl ether sulfate (an ethoxylated anionic surfactant) in combination with an anti-dandruff agent. Typical anti-dandruff agents used in hair care are metal pyrithione e.g zinc pyrithione (ZPTO), Octopirox® (piroctone olamine), azole antimicrobials (e.g. climbazole), selenium sulfide and combinations thereof.

While the problem of dandruff is mitigated to a large extent through use of the above actives in such shampoos, there is a need for enhancing the efficacy, so that not only is the implicated fungal agent minimized during the wash process but the regrowth of the fungi after the washing, is inhibited for a long time thereafter, thereby ensuring dandruff-free scalp and hair to the consumer on a sustained basis.

The present inventors have found that the above requirement is met by the synergistic action of a traditional anti-fungal agent zinc pyrithione in combination with a phenolic compound found in natural plant extract viz. thymol when they are compounded in a shampoo composition comprising synthetic anionic surfactant.

WO2004/006876 (Unilever) discloses a hair and/or scalp treatment composition comprising tulsi oil and a metal pyrithione, wherein the tulsi oil and the metal pyrithione are capable of exhibiting a synergistic antimicrobial activity.

WO2010/046238 (Unilever) discloses compositions comprising selected ingredients namely thymol and terpineol which have relatively fast antimicrobial action.

The above publications do not disclose the synergistic actives of the present invention and further do not disclose the inhibition of the anti-microbial activity for a long time after washing the hair/scalp with a shampoo composition.

It is thus an object of the present invention to provide for a personal cleansing composition that not only exhibits enhanced anti-fungal efficacy but ensures inhibition in the growth of the microbes long after the washing process is complete.

SUMMARY OF THE INVENTION

According to the first aspect of the present invention there is an anti-microbial cleansing composition comprising from:
(i) 0.1 to 30% by weight of a synthetic anionic surfactant;
(ii) 0.1 to 3.0% by weight of zinc pyrithione; and
(iii) 0.01 to 2.0% by weight of thymol, wherein said composition is an anti-dandruff hair care composition.

The second aspect of the present invention relates to a method of providing anti-microbial efficacy to skin comprising the steps of applying a composition of the first aspect on to the desired skin surface which is hair or scalp, followed by rinsing the surface with water.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. In other words, in specifying any ranges of values, any particular upper value can be associated with any particular lower value.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

By 'An Antimicrobial Cleansing Composition' as used herein, is meant to include a composition for topical application to skin, hair and/or scalp of mammals, especially humans. Such a composition is generally applied on to the desired topical surface of the body and then preferably rinsed off, in a few minutes thereafter. It includes any product applied to a human body for also improving appearance, cleansing, odor control or general aesthetics. The composition of the present invention can be in the form of a liquid, lotion, cream, foam, scrub, gel, or bar. Non-limiting examples of such compositions include wash-off shampoos, conditioners shower gels, hand wash liquids or gels or bars. The composition of the present invention is most preferably a shampoo.

The present invention relates to an antimicrobial cleansing composition. A preferred aspect is an anti-dandruff hair care composition. It comprises synergistic anti-fungal action of zinc pyrithione and thymol in the presence of an anionic surfactant.

The composition comprises antidandruff agent zinc pyrithione. Zinc pyrithione (ZPTO) is shorthand for zinc 1-hydroxy-2-pyridinethione.

The metal pyrithione are generally represented by the following general formula:

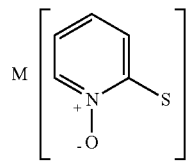

In the case of zinc pyrithione, M is the metal cation zinc.

Zinc pyrithione is preferably present in 0.1 to 2.0%, more preferably from 0.1 to 1.5% based on weight of the composition. ZPTO is a particulate material. While the particle size is not critical to achieve the benefits of the present invention, the particle size of ZPTO is preferably from 0.25 to 8 micrometer, more preferably from 0.5 to 8.0 micrometer, and further more preferably from 1.0 to 7.5 micrometer. ZPTO is commercially available from Kolon Life Science Inc., Sino Lion (USA) Ltd, Lonza, and other suppliers.

The hair care composition comprises 0.01 to 2%, preferably 0.01 to 1.5%, more preferably 0.05 to 1%, and most preferably 0.1 to 1.0% thymol by weight of the composition. Most of the useful compositions of the present invention have thymol higher than 0.2 and lesser than 1.0% by weight thymol. Thymol may be added to the antimicrobial composition in purified form.

Alternatively, thyme oil or thyme extract comprising thymol may be added to the antimicrobial composition, while ensuring that thymol is present in the desired concentration in the composition of the present invention. Thyme oil or thyme extract is obtained from the thyme plant. Thyme plant refers to a plant belonging be genus *Thymus* and includes but is not limited to the following species: *Thymus vulgaris, Thymus zygis, Thymus satureoides, Thymus mastichina, Thymus broussonetti, Thymus maroccanus, Thymus pallidus, Thymus algeriensis, Thymus serpyllum, Thymus pulegoide*, and *Thymus citriodorus*.

The structures of thymol and its isomer carvacrol are given below:

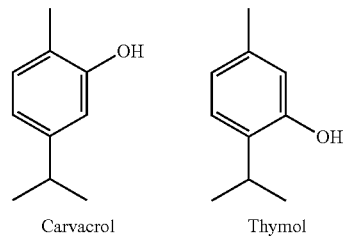

Carvacrol Thymol

As per an especially preferred aspect of the invention, the composition is a shampoo. The composition of the invention especially shampoos are formulated with an anionic surfactant e.g. an alkyl sulphate and/or ethoxylated alkyl sulfate surfactant. These anionic surfactants are preferably present at a level of from 1 to 20%, preferably 2 to 16%, further more preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium.

Preferred alkyl ether sulfates are those having the formula: RO(CHCHO)SOM; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES).

Preferred ethoxylated alkyl sulfate anionic surfactant is sodium lauryl ether sulfate (SLES). SLES having an average degree of ethoxylation of from 0.5 to 3, preferably 1 to 3 is especially preferred.

Shampoo compositions according to the invention may comprise one or more further anionic cleansing surfactants which are cosmetically acceptable and suitable for topical application to the hair.

Examples of further suitable anionic cleansing surfactants are the alkaryl sulphonates, alkyl succinates, alkyl sulphosuccinates, alkyl ether sulphosuccinates, N-alkyl sarcosinates, alkyl phosphates, alkyl ether phosphates, and alkyl ether carboxylic acids and salts thereof, especially their sodium, magnesium, ammonium and mono-, di- and triethanolamine salts. The alkyl and acyl groups generally contain from 8 to 18, preferably from 10 to 16 carbon atoms and may be unsaturated. The alkyl ether sulphosuccinates, alkyl ether phosphates and alkyl ether carboxylic acids and salts thereof may contain from 1 to 20 ethylene oxide or propylene oxide units per molecule.

Typical anionic cleansing surfactants for use in compositions of the invention include sodium oleyl succinate, ammonium lauryl sulphosuccinate, sodium lauryl ether sulphosuccinate, sodium dodecylbenzene sulphonate, triethanolamine dodecylbenzene sulphonate, lauryl ether carboxylic acid and sodium N-lauryl sarcosinate.

Suitable preferred additional anionic cleansing surfactants are sodium lauryl ether sulphosuccinate(n)EO, (where n is from 1 to 3), lauryl ether carboxylic acid (n) EO (where n is from 10 to 20).

Mixtures of any of the foregoing anionic cleansing surfactants may also be suitable.

In a preferred aspect of the present invention, the weight ratio of the zinc pyrithione to the synthetic anionic surfactant is 1:1 to 1:100, preferably 1:2 to 1:50, more preferably 1:5 to 1:30.

It is preferred that the composition does not comprise anionic surfactant from natural sources for examples salts of fatty acids (also known as soaps). If included, salt of fatty acid (soaps) are present in less than 20%, preferably less than 10%, more preferably less than 1% by weight the composition.

A composition of the invention preferably additionally comprises an amphoteric surfactant preferably a betaine surfactant preferably an alkyl amidopropyl betaine surfactant for example cocamidopropyl betaine. In a preferred embodiment, the composition comprises from 0.1 to 10 wt. %, preferably from 0.5 to 8 wt. %, more preferably from 1 to 5 wt. % of a betaine surfactant To enhance deposition of actives from compositions of the invention especially shampoos, cationic polymers are generally included therein. In the present invention too, it is preferred that the composition additionally includes 0.01 to 2.0% of a cationic polymer. The cationic polymer is preferably guar hydroxypropyl trimonium chloride. Guar polymer predominantly contains galactomannan polymer chains. This polymer is available at various molecular weights and degree of cationic substitutions depending on how much the guar has been hydrolysed and cationised. The cationic polymer is preferably present in 0.04 to 0.5%, more preferably 0.08 to 0.25% by weight of the composition.

When conditioning benefits are to be delivered through the composition of the invention the composition comprises a conditioning agent. Typically, the most popular conditioning agents used in hair care compositions are water-insoluble oily materials such as mineral oils, naturally occurring oils such as triglycerides and silicone polymers. Conditioning benefit is achieved by the oily material being deposited onto the hair resulting in the formation of a film, which makes the hair easier to comb when wet and more manageable when dry. An especially useful conditioning agent is a silicone compound, preferably a non-volatile silicone compound. Advantageously compositions herein may include one or more silicones. The silicones are conditioning agents found in dispersed or suspended particulate form. They are intended to deposit onto hair remaining behind after rinsing of the hair with water. Suitable silicone oils may include polyalkyl siloxanes, polyaryl siloxanes, polyalkylaryl siloxanes, polyether siloxane copolymers and mixtures thereof. Amino silicones are often formulated with shampoo compositions. Amino silicones are silicones containing at least one primary amine, secondary amine, tertiary amine or a quaternary ammonium group. High molecular weight silicone gums can also be utilized. Another useful type are the crosslinked silicone elastomers such as DimethiconeNinyl/Dimethicone Crosspolymers (e.g. Dow Corning 9040 and 9041). Amounts of the silicone in compositions where present may range from about 0.1 to about 10 wt. %, preferably from about 0.1 to about 8 wt. %, more preferably from about 0.3 to about 5 wt. % by weight of the hair care compositions.

The pH of the composition is preferably equal to or higher than 4.0, more preferably in the range of 5.0 to 7.0.

The composition as per the invention especially for anti-dandruff shampoos preferably additionally comprises a zinc compound. The presence of additional zinc compound in the composition is believed to improve the antidandruff efficacy of the zinc based antidandruff agent. Suitable zinc compounds are zinc oxide, zinc citrate, zinc malonate, zinc carbonate or combinations thereof. The zinc compound is preferably present in 0.1 to 3%, more preferably 0.1 to 1.5% by weight of the composition.

Shampoo composition as per the invention preferably additionally comprises a conazole fungicide. Preferably the conazole fungicide is selected form ketoconazole, climbazole or mixtures thereof. The azole fungicide is preferably included in 0.01 to 2%, more preferably 0.025 to 0.75% by weight of the composition. The presence of a conazole fungicide is believed to improve the deposition of zinc pyrithione.

The composition preferably additionally comprises a vitamin B3 compound. The preferred vitamin B3 compound is niacinamide.

Niacinamide has the structure as given below

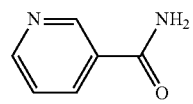

Niacinamide is known for secretion of AMPs from keratinocytes. The AMPs thus secreted provides for improving the immunity of the external surface of the body e.g. on the scalp. Thus with the use of niacinamide in the composition of the invention the anti-dandruff efficacy is expected to be enhanced not just through anti-fungal activity of the composition of the invention but by providing a boost to the scalp's own protection shield against germs, through use of niacinamide. It is expected that this combination could provide further long-lasting protection e.g. up to 24 hours of protection against germs. Niacinamide is preferably present in 0.1 to 5%, more preferably 0.5 to 5%, further more preferably 0.5 to 3%, and optimally 1.0 to 3.0% by weight of the composition.

Suspending Agent

Preferably the composition of the invention further comprises a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolam ides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative.

Suspending agent, if included, will generally be present in a shampoo composition of the invention at levels of from 0.1 to 10%, preferably from 0.5 to 6%, more preferably from 0.5 to 4% by total weight of suspending agent based on the total weight of the composition.

A composition of the invention may contain other ingredients for enhancing performance and/or consumer acceptability. Such ingredients include fragrance, dyes and pigments, pH adjusting agents, pearlescers or opacifiers, viscosity modifiers, preservatives, and natural hair nutrients such as botanicals, fruit extracts, sugar derivatives and amino acids.

The composition of the invention is preferably aqueous based. It preferably comprises high amounts of water preferably from 70 to 95% by weight of the composition.

The present invention also relates to a method of providing anti-microbial efficacy to skin comprising the steps of applying a composition of the invention on to the desired skin surface which is hair or scalp, followed by rinsing the surface with water. The step of rinsing is generally carried out within 1 to 5 minutes after application of the composition on the hair/scalp. According to one aspect, the invention provides for non-therapeutic benefits.

The invention will now be illustrated with reference to the following non-limiting Examples.

Examples

The following base shampoo formulation was prepared (BASE 1)

| Ingredient (% active in water) | INCI name | Wt % |
| --- | --- | --- |
| SLES.1EO (27.04%) | Sodium Laureth Sulfate | 51.8 |
| CAPB (30%) | Cocamidopropyl Betaine | 5.3 |
| Cationic Guar | Guar Hydroxypropyltrimonium Chloride | 0.2 |
| DC 7128(60%) | Dimethicone and Laureth-4 and Laureth-23 and Poloxamer 407 | 1.3 |
| DC1788(50%) | Dimethiconol and TEA-Dodecylbenzene Sulfonate | 2.4 |
| Sodium Hydroxide | Sodium Hydroxide | 0.7 |
| Carbopol 980(3%) | Carbomer | 20.0 |
| NaCl | Sodium Chloride | 0.5 |
| Water | water | To 100 |

Various compositions were prepared as shown in Table-1 below. Example 1 is not a shampoo composition but involves washing simply with water. In Examples 2 to 6, to the base composition BASE1, various amounts of ZPTO and/or thymol were added.

The invention claimed is:

1. An antimicrobial cleansing composition comprising from:
   (i) 0.1 to 30% by weight of a synthetic anionic surfactant selected from the group consisting of an alkyl sulphate, an ethoxylated alkyl sulfate surfactant and mixtures thereof;
   (ii) 0.5 to 1% by weight of zinc pyrithione; and
   (iii) 0.5 to 1% by weight of thymol, wherein said composition is an anti-dandruff hair care composition.

2. The composition of claim 1, wherein the weight ratio of the zinc pyrithione to the synthetic anionic surfactant is 1:1 to 1:100.

3. The composition of claim 1, wherein the composition comprises less than 20 weight % salt of fatty acid.

4. The composition of claim 1, wherein the composition is a shampoo.

5. The composition of claim 1, wherein the synthetic anionic surfactant is sodium lauryl sulphate.

6. The composition of claim 1, additionally comprising an amphoteric surfactant.

7. The composition of claim 1, additionally comprising 0.01 to 2.0% of a cationic polymer.

8. The composition of claim 7, wherein the cationic polymer is guar hydroxypropyl trimonium chloride.

9. The composition of claim 1, additionally comprising 0.1 to 10% by weight of a silicone compound.

10. The composition of claim 1, additionally comprising a vitamin B3 compound.

11. The composition of claim 1, additionally comprising 70 to 95% water.

12. A method of providing anti-microbial efficacy to skin comprising applying a composition of claim 1 on to the desired skin surface which is hair or scalp; and rinsing the surface with water.

* * * * *